United States Patent [19]

Walker

[11] Patent Number: 4,637,382

[45] Date of Patent: Jan. 20, 1987

[54] MOTION-GUIDING LOAD-BEARING EXTERNAL LINKAGE FOR THE KNEE

[75] Inventor: Peter S. Walker, Weston, Mass.

[73] Assignee: Brigham & Women's Hospital, Boston, Mass.

[21] Appl. No.: 642,716

[22] Filed: Aug. 22, 1984

Related U.S. Application Data

[63] Continuation of Ser. No. 372,109, Apr. 27, 1982, abandoned.

[51] Int. Cl.$^4$ .............................................. A61F 5/04
[52] U.S. Cl. .................................. 128/92 Z; 623/39; 128/80 F
[58] Field of Search .................. 128/92 Z, 92 AB, 88, 128/83, 84 B, 84 C, 85; 623/39

[56] References Cited

U.S. PATENT DOCUMENTS

| | | | |
|---|---|---|---|
| 522,143 | 6/1894 | Behrens . | |
| 911,243 | 2/1909 | Johannesen . | |
| 1,390,915 | 9/1921 | Loth . | |
| 1,975,040 | 9/1934 | Groves . | |
| 2,883,982 | 4/1959 | Rainey . | |
| 3,552,786 | 1/1971 | Schmid . | |
| 3,779,654 | 12/1973 | Horne | 128/80 X |
| 3,826,251 | 7/1974 | Ross | 128/80 F |
| 3,837,009 | 9/1974 | Walker | 623/20 |
| 3,902,482 | 9/1975 | Taylor | 128/80 F |
| 3,941,123 | 3/1976 | Volkvo et al. | 128/84 B |
| 3,976,061 | 8/1976 | Volkov et al. | 128/84 B |
| 4,005,496 | 2/1977 | Wilkes | 623/39 |
| 4,139,002 | 2/1979 | Almedia | 128/80 C |
| 4,241,730 | 12/1980 | Helfet | 128/80 C |

FOREIGN PATENT DOCUMENTS

| | | | |
|---|---|---|---|
| 855611 | 11/1952 | Fed. Rep. of Germany . | |
| 2152408 | 10/1971 | Fed. Rep. of Germany | 623/39 |
| 478031 | 2/1953 | Italy | 623/39 |

OTHER PUBLICATIONS

Robert Foster et al., Orthotic/Prosthetic/Orthopedic Aids.
Volkov, et al., The Journal of Bone and Joint Surgery, Jul. 1975.
Anthony Staros, Director, VAREC Review.
Use of the Hoffmann Apparatus in the Treatment of Unstable Tibial Fractures by Ruskin B. Lawyer, Jr., M.D. and Lawrence M. Lubbers.
An in Vivo Biomechanical Evaluation of Anterior-Posterior Motion of the Knee by Peter A. Torzilli, Ph.D., et al.
In Vivo Knee Stability, A Quantitative Assessment Using an Instrumented Clinical Testing Apparatus by Keith L. Markolf, Ph.D.
Knee Morphology as a Guide to Knee Replacement by Joseph S. Mensch, M.D. and Harlan C. Amstutz, M.D.
Ligament Length Pattersn, Strength, and Rotational Axes of the Knee Joint by Peter S. Trent, M.S., et al.
Conformity in Condylar Replacement Knee Prostheses by P. S. Walker, Ph.D and H. H. Hsieh.
Investigations into the Mechanical Behaviour of Bone--Pin Connections by E. J. Klip and R. Bosma.
A Three-Dimensional Study of the Kinematics of the Human Knee by P. A. Blacharski and J. H. Somerset.

*Primary Examiner*—Richard J. Apley
*Assistant Examiner*—David J. Isabella
*Attorney, Agent, or Firm*—Saidman, Sterne, Kessler & Goldstein

[57] ABSTRACT

A motion guiding load bearing external linkage for a knee is provided by plates fixed to the medial and lateral sides of the tibia and femur by transcutaneous pins or incorporated in a knee brace fitting above and below the knee joint. The tibial plates have a planar load bearing surface while the femoral plates have a circular load bearing surface. Linkages are provided for guiding the center of rotation of the femoral load bearing surfaces in the direction of the tibial load bearing surfaces as a function of the degree of knee flexure. This linkage comprises an extension of the tibial plate having a slot which engages a pin fixed to the femoral plate at a point off-set from the center of rotation. This linkage positively guides the motion of the center of rotation along a single path which is predetermined by the radial and annular position of the pin. The guidance characteristics of the predetermined path can be determined to fit the lateral and medial sides of an individual knee by the proper positioning of the pin.

10 Claims, 8 Drawing Figures

MOTION-GUIDING LOAD-BEARING EXTERNAL LINKAGE FOR THE KNEE

This application is a continuation, of application Ser. No. 372,109, filed Apr. 27, 1982 now abandoned.

BACKGROUND OF THE INVENTION

1. Field of the Invention

The present invention relates to external motion-guiding linkages for a human knee. More particularly, the present invention relates to an external motion-guiding load-bearing external linkage which can be positioned to accurately guide the motion of the knee while closely replicating normal motion and can be adjusted to either carry a required portion of the load or to distract and unload the knee completely.

2. Brief Description of the Prior Art

The knee joint is subject to many types of traumatic injuries and pathological conditions which result in soft tissue rupture, dislocation, bone fracture, cartilage erosion, or infection. The present methods of treatment are usually rest, bracing, casting, internal fixation, external fixation, ligamentous reconstruction, prosthetic replacement or a combination of the above.

Immobilization has been found to be less than satisfactory because it can reduce subsequent motion of the joint sometimes permanently. Soft tissue repairs are adversely affected by both immobilization and mobilization, unless the latter is prevented from overstretching the tissues before healing occurs. Internal fixation has the shortcoming that a long period of non-weight bearing is often necessary before adequate bone strength is achieved.

External linkages would not suffer from the above shortcomings but have been unsatisfactory in the past because they provide only approximate motion and are not compatible with the more exacting motion requirements of the internal structures of the knee. A system which accurately controls the motion of the knee and which allows a required amount of load-bearing would thus be of great clinical benefit and would enable further advances in surgical treatment.

However, accurately replicating the internal motions of the knee has been difficult because the motion of the knee cannot be represented as a simple fixed-axis hinge. Rather, it has been known that the joint surfaces of the knee undergo a combination of rolling and sliding, that the medial and lateral sides move differently and that there is a transverse rotation of the femur about the longitudinal axis of the tibia, especially towards the extension position. This is known as the "screw-home" mechanism.

The above can best be understood with reference to FIG. 1 which is a schematic representation of the joint as seen from the medial or lateral side. As seen there, the tibia 2 includes upper joint load-bearing surfaces 4 which are slightly curved and slope downward in a posterior direction by about 10° relative to the longitudinal axis 6 of the tibia. The femur includes lateral and medial condyles whose load-bearing surface outlines can be approximated by circular arcs. That is, the centers of curvature of those portions of the load-bearing surface 10 which are in contact with the tibia at various angles of flexure are not identical. As seen in FIG. 1, at small degrees of flexure, the arc BC which is defined by the load-bearing surface has a center of curvature A. However, at greater flexure of the knee (dashed line position) the arc BD defined by the load-bearing surface has a center of curvature P which is different from A. Thus, a simple hinge having a single center of rotation would not accurately represent the complex motion of the knee joint.

Attempts have been made in the prior art to describe this knee flexion, extension motion by charting the path of the instant centers of rotation of the surface 10. In some cases, smooth curves were found while in others erratic curves were found. In any case, all of the plotted movements of the centers of rotation differed from knee to knee and from the medial to the lateral sides of a given knee. It has also been discovered that the instantaneous center of rotation of the surface 10 could be accurately represented by the rolling of fixed and moving centrode paths of simple geometry.

This concept of rolling one surface on another was utilized in the structure disclosed in "Restoration of Function in the Knee and Elbow with a Hinge Distractor Apparatus" by Volkov et al (see *The Journal Of Bone and Joint Surgery*, Vol. 57-A, No. 5, July 1975, pp. 591 to 600). In the design there described, two transverse pins through the femur and tibia held an adjustable rack and pinion on the medial and lateral sides as well as a locking mechanism anteriorly. Traction bows encircled the anterior halves of the shank and thigh. The rack and pinion arrangement utilized the concept of rolling one surface on another. However, this design was complex and did not accurately approximate the motion of the knee. The rack and pinion resulted in backward motion of the femoral condyles on the tibial condyles during flexion. Moreover, there were no differences in motion between the medial and lateral sides of the joint. A further problem was that varus and valgus were controlled statically by anterior locking bars, but not dynamically.

Orthotic devices generally used today employ a simple fixed-axis metal or plastic hinge set as close to the average center of rotation as possible, or a "polycentric" hinge similarly placed. These joints, as with Volkov et al, do not account for medial/lateral differences and for transverse rotation. The transverse rotation is taken up by the looseness in the device and by the soft tissues between the clamped device and the bone. None of the orthotic devices in use provide for more than approximate methods of placement. However, such is not possible when using transcutaneous pins which are fixed to the bone itself, and an external frame mounted on transcutaneous pins must allow for very accurate approximations of the knee motion.

SUMMARY OF THE INVENTION

It is an object of the present invention to provide an external motion guiding load-bearing linkage for the knee which accurately and positively guides the motion of the knee and carries a required portion of the load.

According to the present invention, the tibia load-bearing surface 4 is simulated as a planar surface in the direction x (FIG. 1) while the femoral condylar load-bearing surfaces are simulated as circular load bearing surfaces having centrodes moving from point P to point Q during the flexure of the knee (FIG. 1). That is, it has been determined that the rolling and sliding motion of the knee joint causes the centrode to move from P to Q during flexure, the distance PQ varying between the lateral and medial sides. Thus, the present invention attempts to provide a structure which guides the center of rotation of the circular load-bearing surfaces from point P to point Q.

The present invention simulates the load bearing surfaces 4 and 10 by providing plates mounted to the medial and lateral sides of the tibia and femur, possibly by transcutaneous transverse pins, but possibly by incorporating in a well-fitting brace. The tibial plates have planar load-bearing surfaces extending approximately parallel to and in the plane of the upper surface of the tibia as determined by radiographic views and palpation. The femoral plates have load-bearing surfaces in the form of circular arcs resting upon the load-bearing surface of the tibial plates, the positions of the femoral plates being determined by radiographic views and palpation such that the arcs overlap the positions of the femoral condyles with sufficient vertical adjustment for the desired portion of the load which the plates are to carry. The tibial plates includes axial extensions having slots within which slide pins fixed to the femoral plates. The pins are off-center from the center of rotation of the circular arcs so that, as the knee is flexed, the tibial and femoral plate load-bearing surfaces will undergo a combination of rolling and sliding motion, the precise proportions of rolling and sliding depending upon the angular and radial position of the pin relative to the center of rotation. The effect of the rolling and sliding motion is to move the center of rotation of the circular femoral plate-bearing surface posteriorly relative to the tibial load-bearing surface at a rate simulating the movement PQ of the centrode of a normal knee. By preselecting the radial and angular positions of the eccentric pins mounted on the femoral plate, it is possible to tailor the guiding motion of the linkage to characteristics of a selected knee. Thus, by measuring the motion patterns of an individual's knee during flexure, one can custom fit linkage to provide motion patterns for the medial and lateral condyles, or one can provide a motion pattern from a range of available sizes which best fit the measured motion pattern of the medial or lateral condyle of an individual. Thus, not only can individual knees be accommodated so as to provide the precise guidance necessary, but it is possible to easily provide separate guidance paths for the lateral and medial sides of a given knee. If one knee of a patient is damaged, the motion of the other knee will be measured and assumed to be similar to that of the damaged knee. If both knees are inaccessible, average knee motions, known from lab studies, will be used.

The slot in the tibial extensions will allow some varus or valgus to occur. If this is undesirable, varus or valgus can be controlled by a second horizontal slot in the extension plate in alignment with a pin extending from the center of rotation of the femoral plate bearing surface.

BRIEF DESCRIPTION OF THE DRAWINGS

Various other objects, features and attendant advantages of the present invention will be more fully appreciated as the same become better understood from the following detailed description when considered in connection with the accompanying drawings in which like reference characters designate like or corresponding parts throughout the several views and wherein.

DETAILED DESCRIPTION OF THE PREFERRED EMBODIMENTS

Figure 1:
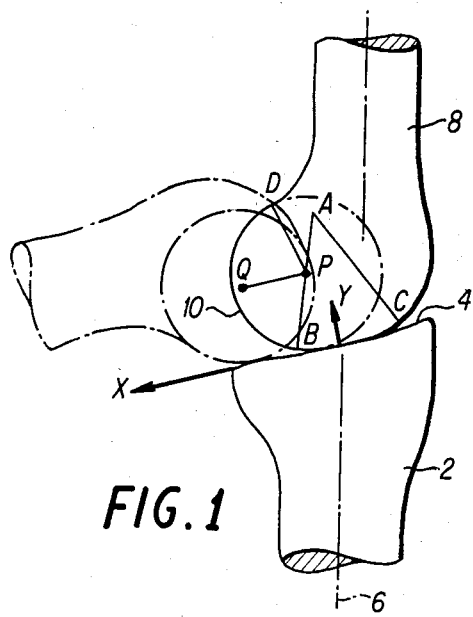
FIG. 1 is a schematic illustration, from the lateral or medial side, of a knee joint.
Figure 2:
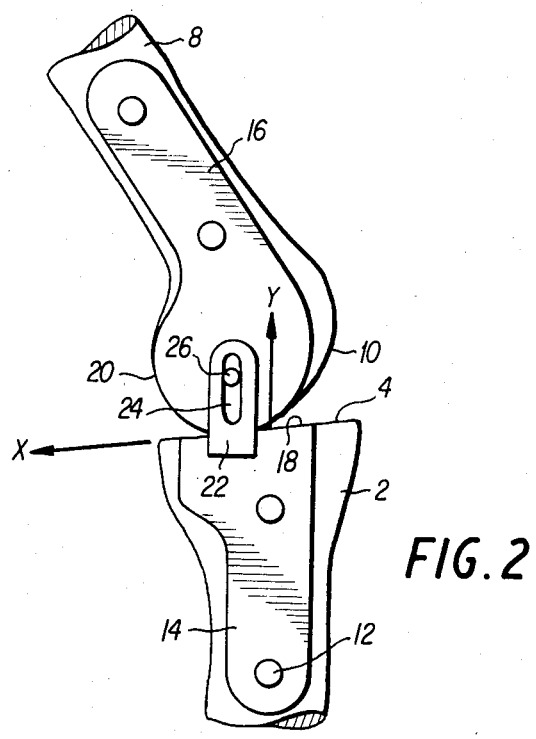
FIG. 2 is a schematic illustration from the lateral or medial side, of the apparatus according to the present invention.
Figure 3:
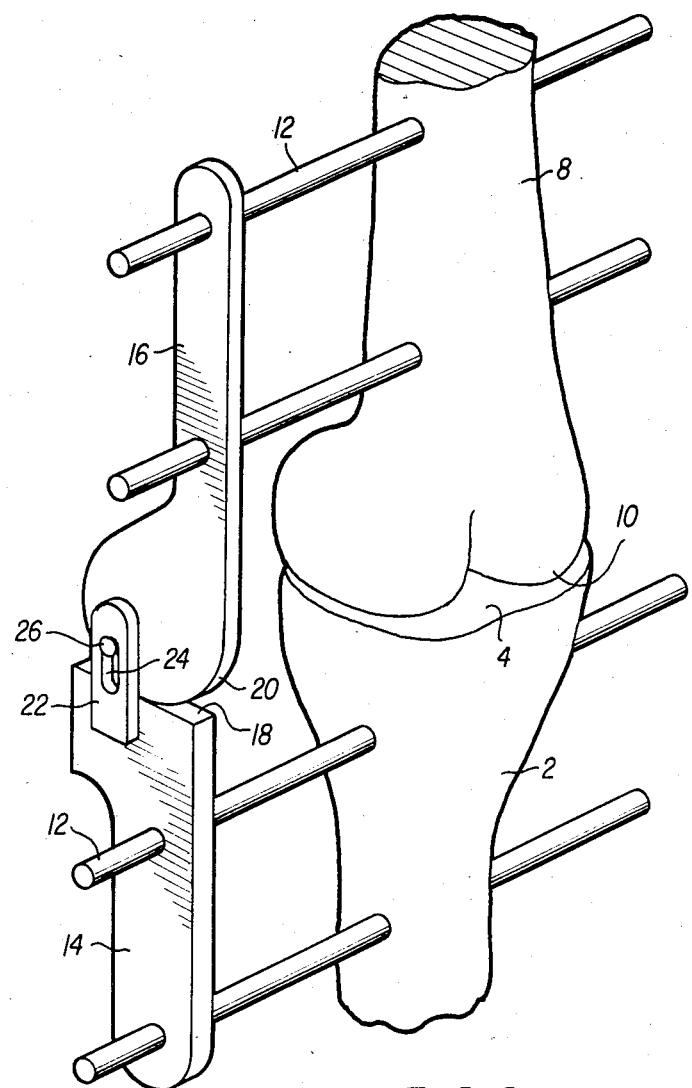
FIG. 3 is an exploded orthogonal view of one side of one embodiment of the apparatus of the present invention.

As best seen in FIGS. 2 and 3, in a first embodiment, transcutaneous transverse pins 12 secure tibial plates 14 and femoral plates 16 to the medial and lateral sides of the joint. Only one side is shown, however the other side would be similar except for the positioning of the pin and shape variations of the load-bearing surfaces. The plates 14 and 16 are made from a metal such as stainless steel or titanium alloy and the upper load-bearing surface 18 of the tibial plate is preferably formed from a plastic material such as RCH 1000 high molecular weight polyethylene to minimize friction and wear. The transcutaneous pins 12 are formed of metal and are of a type which is well known in the art.

The upper load-bearing surface 18 of each tibial component is essentially planar along the direction x and supports the circular load-bearing surface 20 of the femoral plate 16. The structure can be adjusted so that the load-bearing surfaces support part or all of the load of the knee with the remainder being borne by the knee joint itself.

In order to provide the desired polycentric motion of the circular surface 20 on the planar surface 18, a linkage is provided for guiding the motion of the load-bearing surfaces relative to one another such that the center of rotation of the circular surface 20 is moved posteriorally by a desired amount during the flexure of of the knee. This linkage consists of an extension 22 of the tibial plate which extends upward from the surface 18 in the direction y transverse to the surface 18. The extension 22 includes a longitudinal slot 24 which engages a pin 26 extending transversely from the femoral plate 16 at a point off-set from the center of rotation of the circular bearing surface 20.

Figure 4:
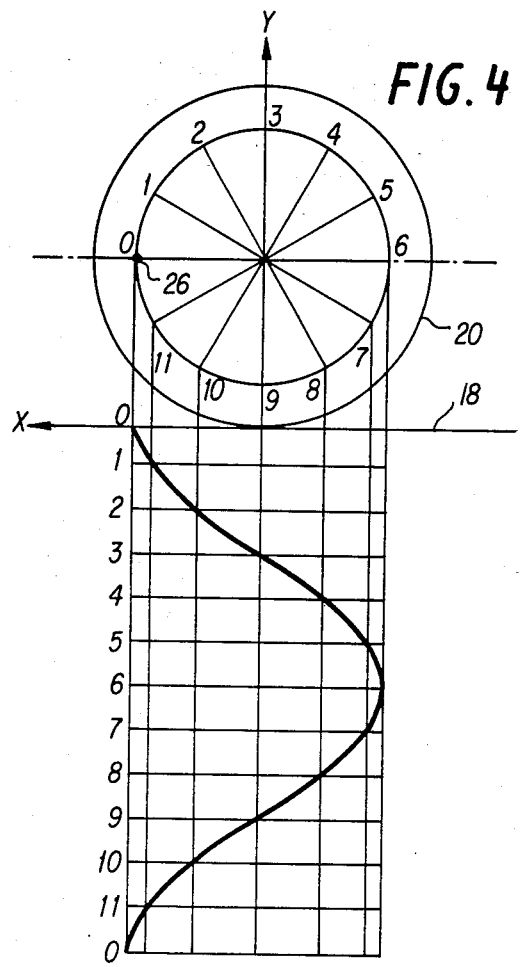
FIG. 4 is a schematic illustration of the degree of movement of the center of rotation of a knee joint at various degrees of flexion.

The pin and slot arrangement permits the pin to move in the direction y but not in the direction x relative to the tibial plate 14. The effect of this can best be seen with reference to FIG. 4. In FIG. 4, the outer circle schematically represents the circular surface 20 while the inner circle schematically represents the radius r of a pin 26 which may be positioned at any of the annular positions 0-11. At position 0, the pin is off-set from the center of rotation only in the direction x. Upon knee flexure, a small angular change of position of the pin 26 will be almost entirely in the direction y and will be permitted by the motion of the pin 26 within the slot 24. Thus, there will be almost entirely sliding motion between the surfaces 18 and 20 and very little rolling motion between the surfaces 18 and 20. However, further angular rotation of the pin to position 3, due to further knee fluxure, will result in the motion of the pin being almost entirely in the direction x. Motion in the direction x is prevented by the slot and thus some of the sliding motion is replaced by rolling motion as a trigonometric function of the angle of rotation. The maximum total relative rolling of the surfaces 18 and 20, which represents the maximum shifting of the center of rotation in the direction x, is a function of the distance r of the pin from the center of rotation of the surface 20.

Figure 5:
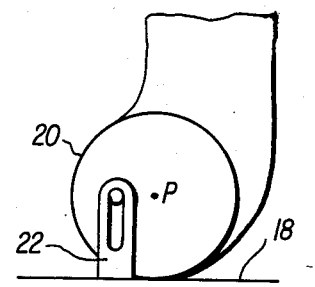
FIGS. 5a and 5b are schematic illustrations of the apparatus of the present invention in the unflexed and fully flexed positions.
Figure 5:
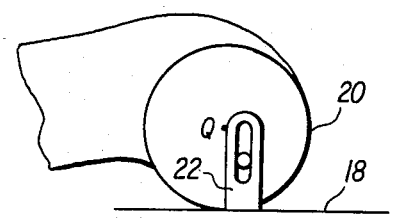

For example, FIG. 5a schematically illustrates the knee in the unflexed position wherein the pin is at annular position 0 and the center of rotation P of the circle 20 is relatively anterior of the extension 22. However, FIG. 5b shows the knee in the fully flexed position wherein the center of rotation has moved to Q at the left of the extension 22 and is relatively posterior thereto upon the surface 18. Thus, by preselecting the radius r and the angular position of the pin in the unflexed knee position, one can custom tailor the movement of the center of rotation so as to approximate that of a given knee condyle and thus positively guide the motion of the bearing surfaces along a predetermined path.

Figure 6:
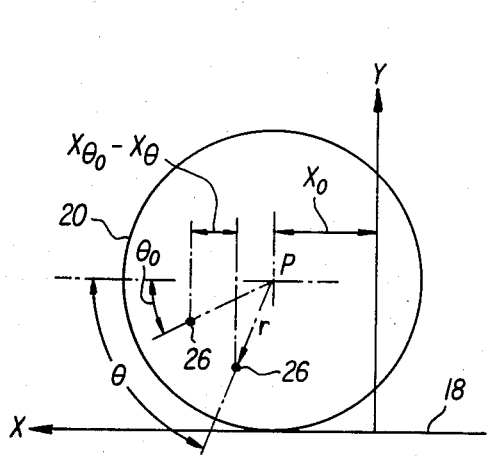
FIG. 6 is a schematic diagram illustrating the positioning of the pin on the femoral plate.

If we consider the initial position of the center of rotation P to be $x_0$ and if we consider the initial position of the pin 26 to be $x\theta_0$ along the direction x and at a distance R from $x_0$ (FIG. 6), then the movement of $x_0$ in the x direction ($x\theta$) for a rotation of $\theta - \theta_o$ may be found from the equation:

$$x\theta = x_0 + r(\cos \theta_0 - \cos(\theta_0 + \theta)) \quad (1)$$

If the actual value of $x\theta$ for a knee joint is $Ax_\theta$, then the error of the linkage is $Ax_\theta - x_\theta$. Hence, for given values of $\theta_o$ and r, the errors at each 15° arc of flexion up to 120°, can be computed. This computation can be provided by a computer program to which are applied the medial and lateral side data for a given knee. From preliminary studies, it is expected that for the lateral side, $\theta_o$ will be in the range of 0° to 60° and r will be in the range of 10 to 15 mm; and for the medial side, $\theta_o$ will be in the range of 150° to 240° and r will be in the range of 0 to 5 mm.

Thus, in the fitting of the linkage of the present invention, the sizes and locations of the femoral and tibial condyles for an individual are determined by radiographic views and palpation, as is the motion of the knee joint during flexure, the motions of the medial and lateral sides of the knee being different to cause the known transverse rotation of the femur about the longitudinal axis of the tibia (screw-home mechanism). Based upon these studies, femoral and tibial plates can be individually made for the user or plates from preselected sizes can be selected and fitted. The fitting of the plates is adjusted so that a desired portion of the load of the knee is taken up by the bearing surfaces of the plates. The positions of the pins 26 on the lateral and medial sides are then determined from the equation (1) so that the articulation of the linkage, on either side of the knee, closely approximates the knee motions of the user.

Figure 7:
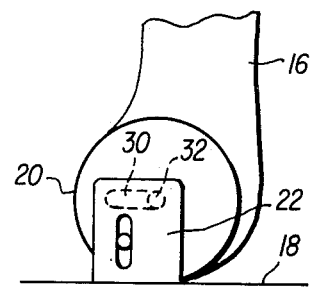
FIG. 7 is a schematic representation of a variation of the apparatus in which a second pin and slot are provided to control varus or valgus.

The pin and slot arrangement of the present invention will, however, allow some varus or valgus to occur. If this is undesirable, the varus and valgus can be controlled by the provision of the structure of FIG. 7. In FIG. 7, a second slot, elongated in the direction x extends only partly through the thickness of the extensions 22 from the surface facing the femoral plate 16. This second slot 30 engages a second transverse pin 32 extending from the femoral plate 16 at the center of rotation of the bearing surface 20. The pins 32 bearing against the ends of the slot 30 have the effect of controlling varus and valgus.

Accordingly, the present invention provides an external linkage which has several important advantages. First, the linkage of the present invention positively guides the motion of the knee through a unique path in which the motions of the medial and lateral sides of the knee are different according to the anatomical motion of the knee in normal knee joints. Second, the present invention carries the load across the knee on strong wear-resistant load bearing surfaces guided by the pins in the slots, the portion of the load being borne by the linkage being adjustable by the fitting during linkage. Third, the linkage can be adjusted for the motion of an individual's knee joint. Finally, the present invention can selectively restrain varus and valgus.

As further features of the present invention, it is possible to provide a locking device to fix the knee at a given angle of flexion, locking the plates 14 and 16. It is also possible to provide a screw adjustment to change this angle for some applications.

Figure 8:
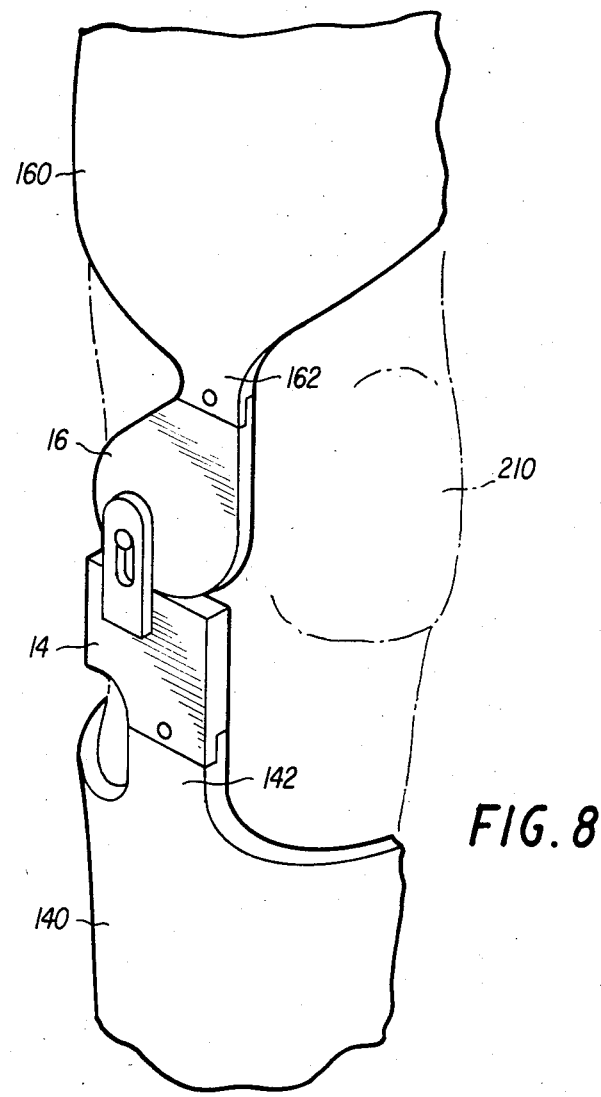
FIG. 8 is an orthogonal view of a portion of another embodiment of the apparatus of the invention.

Since the linkage of the present invention simulates the motion of the knee with sufficient accuracy such that it may be fixed to the knee with transcutaneous pins, it can, of course, also be used with a well fitting knee brace in which inaccuracies are absorbed by soft tissue movement. One possible embodiment of the linkage incorporated into a knee brace is shown in FIG. 8. The knee brace consists of a thigh cuff 160 which is strapped, or otherwise removably secured, to the exterior of a user's thigh and a calf cuff 140 which is similarly removably secured to the exterior of a user's calf. A thigh extension 162 and a cuff extension 142 extend toward one another in the direction towards the user's knee 210. Fixed to the thigh extension 162 is a femoral plate 16 identical to that of the first embodiment. Similarly, a tibial plate 14 such as that of the first embodiment is fixed to the calf extension 142. Procedures for fitting the linkage of FIG. 8 are similar to those for the first embodiment.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters of the United States is:

1. A motion guiding, load bearing, external linkage for a knee joint, comprising:
    first and second tibial components respectively secured to the lateral and medial sides of the tibia, each said tibial component having a tibial load bearing surface;
    first and second femoral components respectively secured to the lateral and medial sides of the femur, each said femoral component having a femoral load bearing surface movably contacting one of said tibial load bearing surfaces; and
    first and second link means respectively connected between said first tibial and femoral components and said second tibial and femoral components, wherein said first and second link means comprise, respectively, first means for positively guiding the relative motion of said first tibial and femoral components along a first predetermined path during knee flexure and second means for positively guiding the relative motion of said second tibial and femoral components along a second predetermined path during knee flexure, said second predetermined path being geometrically different from said first predetermined path, and wherein said first and second means for positively guiding said first and second tibial and femoral components collectively comprise means for forcing transverse rotation of the femur about the longitudinal axis of the tibia during knee flexure.

2. The linkage of claim 1 wherein each of said tibial load bearing surface is substantially planar in the direction from the anterior to the posterior side of the knee, and wherein each said femoral load bearing surface comprises a circular surface extending in the direction from the anterior to the posterior side of the knee.

3. The linkage of claim 1 including transcutaneous transverse pins respectively securing said first and second tibial and femoral components to said tibia and said femur.

4. The linkage of claim 2, wherein said means for positively guiding are constructed such that said first and second predetermined paths comprise both rolling and sliding relative motion of said first and second tibial and femoral load bearing surfaces whereby the center of rotation of each said circular femoral surfaces is shifted in the direction parallel to said planar tibial load bearing surfaces during flexure of said knee.

5. The linkage of claim 4 wherein said first and second means for guiding comprise:
first and second pins extending transversely from said first and second femoral components, respectively, each said first and second pin being spaced from the center of rotation of the respective circular surface by predetermined radial first and second distances defining first and second lines at predetermined first and second angles relative to first and second reference lines perpendicular to said first and second planar load bearing surfaces;
first and second extending portions respectively fixed to said first and second tibial components and extending towards said first and second pins in the directions of said first and second reference lines; and
first and second slots in said first and second extending portions, respectively, said first and second slots being elongated in the directions of said first and second reference lines, said first and second pins being movably engaged in said first and second slots;
whereby the relative proportions of said rolling and sliding motions is a function of said predetermined radial first and second distances and said predetermined first and second angles.

6. The linkage of claim 5 wherein values of said predetermined radial distances and said predetermined angles are a function of the characteristics of the knee to which the frame is mounted and are different for the lateral and medial sides of each knee.

7. The linkage of claim 3 including means for adjusting said linkage to bear the full load of said knee joint.

8. The linkage of claim 1 including means for adjusting said linkage to bear none of the load of said knee joint.

9. The linkage of claim 1 including a brace having a thigh cuff and having a calf cuff removably secured to an exterior of a user's leg whereby said first and second tibial components are secured to the tibia, and whereby the first and second femoral components are secured to the femur via said thigh cuff of said brace.

10. The linkage of claims 5 or 6 including:
third and fourth slots in said first and second extending portions, respectively, said third and fourth slots being elongated in the directions of said planar surfaces and being spaced from said planar surfaces by the same distances as are said centers of rotation; and
third and fourth pins extending transversely from said first and second femoral components, respectively, at said centers of rotation, said third and fourth pins being movably engaged in said third and fourth slots, whereby varus and valgus are prevented.

* * * * *